United States Patent
Stevens et al.

(10) Patent No.: US 8,626,463 B2
(45) Date of Patent: Jan. 7, 2014

(54) DATA STORAGE DEVICE TESTER

(75) Inventors: Curtis E. Stevens, Irvine, CA (US);
Lawrence J. Dalphy, Mission Viejo, CA (US)

(73) Assignee: Western Digital Technologies, Inc., Irvine, CA (US)

( * ) Notice: Subject to any disclaimer, the term of this patent is extended or adjusted under 35 U.S.C. 154(b) by 528 days.

(21) Appl. No.: 12/749,243

(22) Filed: Mar. 29, 2010

(65) Prior Publication Data
US 2011/0154112 A1 Jun. 23, 2011

Related U.S. Application Data

(60) Provisional application No. 61/289,934, filed on Dec. 23, 2009.

(51) Int. Cl.
*G01N 37/00* (2006.01)

(52) U.S. Cl.
CPC ..................................... *G01N 37/00* (2013.01)
USPC .......................................................... 702/81

(58) Field of Classification Search
CPC ..................................................... G01N 37/00
USPC .................... 702/81, 117, 118, 182–185, 188
See application file for complete search history.

(56) References Cited

U.S. PATENT DOCUMENTS

| | | | |
|---|---|---|---|
| 5,509,120 A | 4/1996 | Merkin et al. | |
| 5,513,315 A | 4/1996 | Tierney et al. | |
| 5,589,777 A | 12/1996 | Davis et al. | |
| 6,044,423 A | 3/2000 | Seo et al. | |
| 6,285,911 B1 | 9/2001 | Watts, Jr. et al. | |
| 6,397,247 B1 | 5/2002 | Shirakawa et al. | |
| 6,434,498 B1 | 8/2002 | Ulrich et al. | |
| 6,484,226 B1 | 11/2002 | Wallach et al. | |
| 6,493,656 B1 | 12/2002 | Houston et al. | |
| 6,594,721 B1 | 7/2003 | Sakarda et al. | |
| 6,598,183 B1 | 7/2003 | Grieco et al. | |
| 6,615,367 B1 | 9/2003 | Unkle et al. | |
| 6,711,660 B1 | 3/2004 | Milne et al. | |
| 7,171,586 B1 | 1/2007 | Gross et al. | |
| 7,451,355 B1 | 11/2008 | Coatney et al. | |
| 7,516,025 B1 | 4/2009 | Williams et al. | |
| 7,565,523 B2 | 7/2009 | Han | |
| 7,613,591 B2 * | 11/2009 | Khandros et al. ............. 702/188 |
| 8,332,695 B2 | 12/2012 | Dalphy et al. | |
| 8,458,526 B2 | 6/2013 | Dalphy et al. | |
| 2002/0036850 A1 | 3/2002 | Lenny et al. | |
| 2002/0050814 A1 | 5/2002 | Nozu | |
| 2003/0023925 A1 | 1/2003 | Davis et al. | |
| 2004/0030434 A1 | 2/2004 | Schenk et al. | |
| 2005/0030014 A1 | 2/2005 | Green et al. | |

(Continued)

OTHER PUBLICATIONS http://www.tacktech.com/display.cfm?ttid=287, webpage printed on Mar. 29, 2010.

(Continued)

*Primary Examiner* — Edward Raymond

(57) ABSTRACT

A data storage device (DSD) tester is disclosed for testing a DSD. The DSD tester comprises control circuitry operable to receive production line data through an interface, wherein the production line data is related to the DSD. The control circuitry executes a DSD test on the DSD, and transmits failure data generated by the DSD test and the production line data to a failure information database.

50 Claims, 18 Drawing Sheets

(56) References Cited

U.S. PATENT DOCUMENTS

| | | | |
|---|---|---|---|
| 2005/0262383 | A1 | 11/2005 | Sierer et al. |
| 2006/0242459 | A1 | 10/2006 | Hyde, II et al. |
| 2007/0061638 | A1 | 3/2007 | Nishiuchi et al. |
| 2008/0177922 | A1 | 7/2008 | Chow et al. |
| 2008/0198493 | A1 | 8/2008 | Shitara et al. |
| 2009/0037146 | A1* | 2/2009 | Trowbridge et al. .......... 702/184 |
| 2009/0106592 | A1 | 4/2009 | Gross et al. |
| 2010/0031094 | A1 | 2/2010 | Komagome |
| 2011/0055639 | A1 | 3/2011 | Huang et al. |

OTHER PUBLICATIONS

R. Mines, J. Friesen, and C. Yang, "DAVE: A Plug and Play Model for Distributed Multimedia Application Development", In Proceedings of the second ACM international conference on Multimedia (Multimedia '94), ACM, New York, NY, USA, pp. 59-66.

Ramamurthy, H.; Prabhu, B.S.; Gadh, R.; Madni, A.M.; , "Smart Sensor Platform for Industrial Monitoring and Control," 4th IEEE Sensors 2005, Irvine, California, pp. 1116-1119, Oct. 30, 2005-Nov. 3, 2005.

Sherwin, R.M.; , "Memory on the Move," IEEE Spectrum, vol. 38, No. 5, pp. 55-59, May 2001.

* cited by examiner

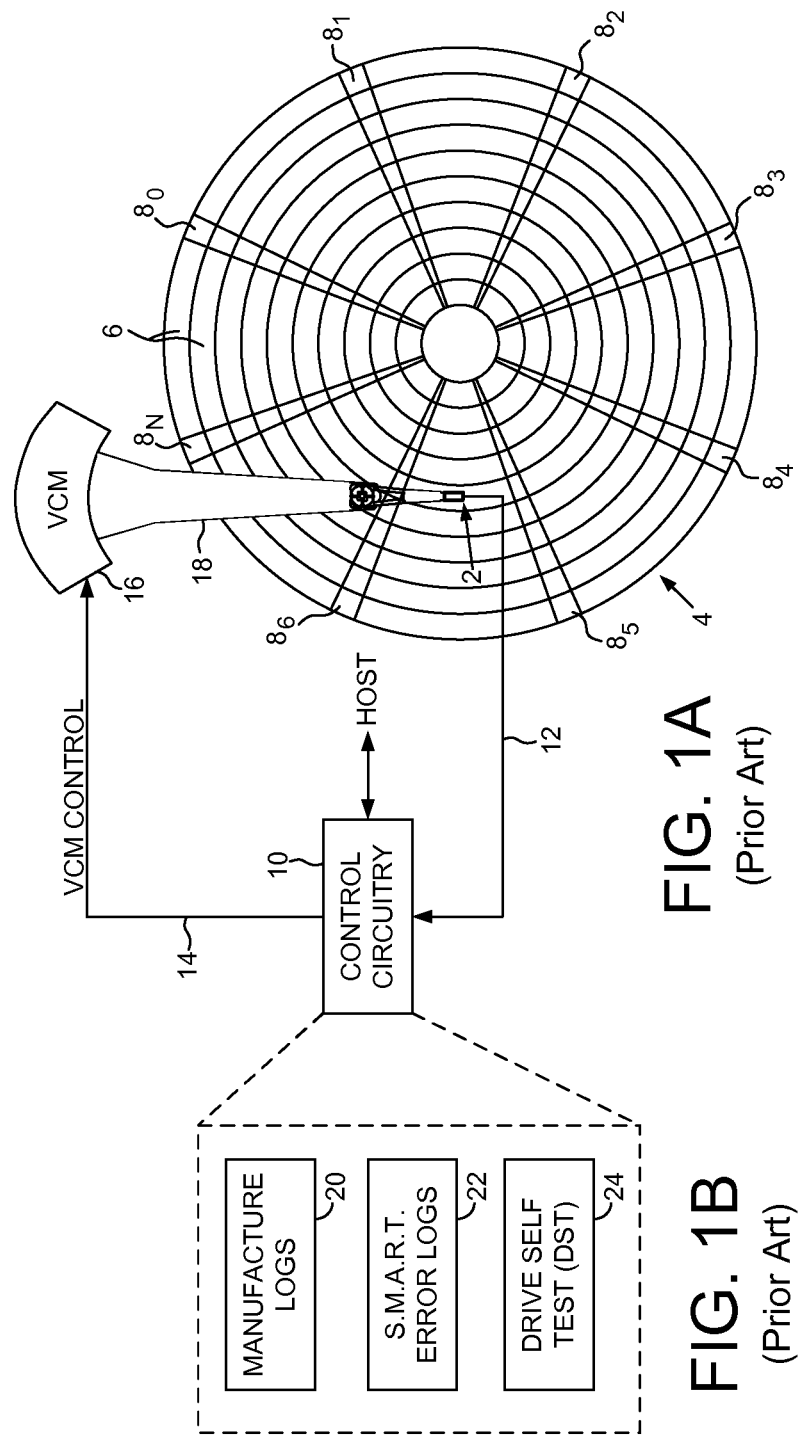

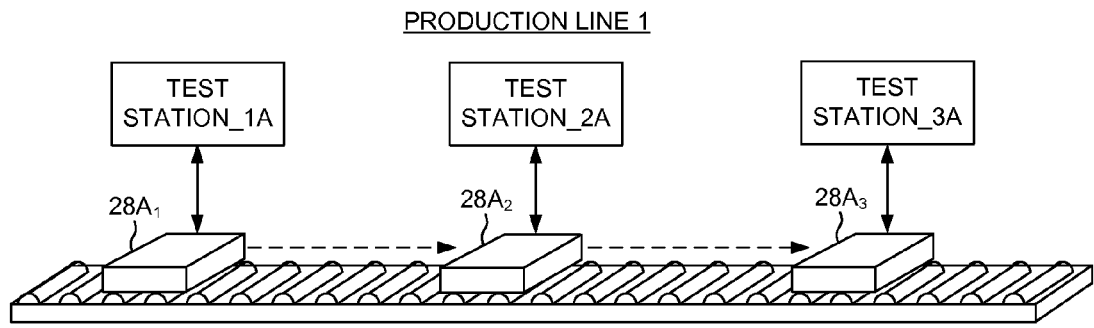
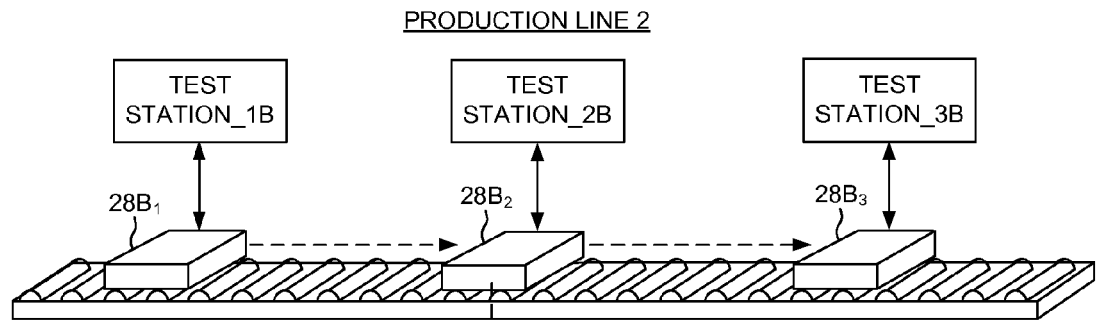
FIG. 2A
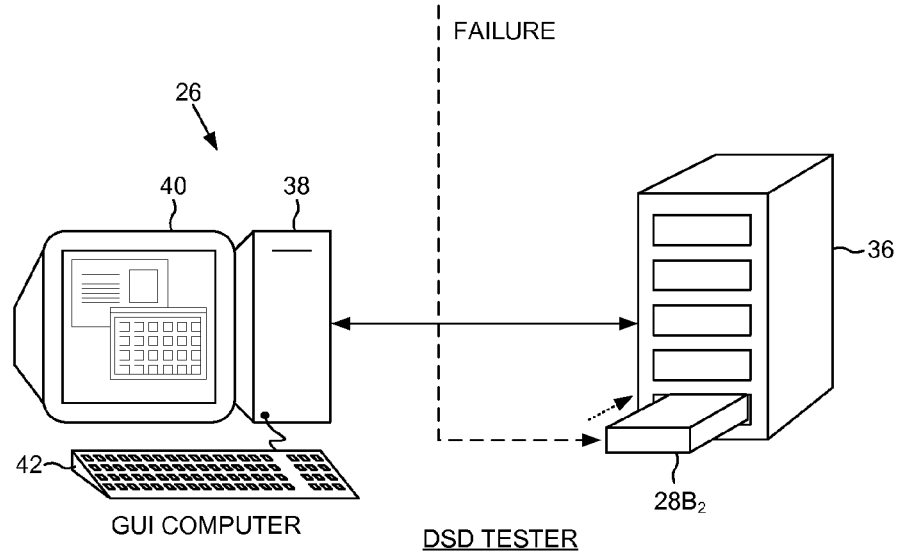
FIG. 2B

```
SERIAL: WMASY6790910                    ( VIEW LOG )  ( CANCEL )
MODEL:  WD6400AAKS
[▨                                                                    ]
STATUS: PERFORMING TEST                 50 MINUTES REMAINING

SERIAL: EMPTY                           ( VIEW LOG )  ( CANCEL )
MODEL:  EMPTY
[                                                                     ]
STATUS: IDLE                            XX MINUTES REMAINING

SERIAL: EMPTY                           ( VIEW LOG )  ( CANCEL )
MODEL:  EMPTY
[                                                                     ]
STATUS: IDLE                            XX MINUTES REMAINING
```

FIG. 4A

```
SERIAL: WMASY6790910                    ( VIEW LOG )  ( CANCEL )
MODEL:  WD6400AAKS
[▨▨▨▨▨▨▨▨▨▨▨▨▨▨▨▨▨▨▨▨▨                                                ]
STATUS: PERFORMING TEST                 29 MINUTES REMAINING

SERIAL: WXE308D84390                    ( VIEW LOG )  ( CANCEL )
MODEL:  WD2500BEVS
[▨                                                                    ]
STATUS: PERFORMING TEST                 50 MINUTES REMAINING

SERIAL: EMPTY                           ( VIEW LOG )  ( CANCEL )
MODEL:  EMPTY
[                                                                     ]
STATUS: IDLE                            XX MINUTES REMAINING
```

FIG. 4B

GUI COMPUTER

USB KEY

DATA STORAGE DEVICE TESTER

CROSS-REFERENCE TO RELATED APPLICATIONS

This patent application claims priority to U.S. Provisional Patent Application Ser. No. 61/289,934, filed Dec. 23, 2009.

BACKGROUND

Description of the Related Art

Data storage devices (DSDs), such as disk drives and solid state drives are employed in numerous applications such as computer systems (e.g., desktops, laptops, portables, etc.) and consumer devices (e.g., music players, cell phones, cameras, etc.). An original equipment manufacture (OEM) will typically purchase DSDs in bulk from a DSD manufacturer for use in the OEM's product. Before and/or after installing the DSD, the OEM will perform a number of tests to verify the DSD is not defective. If a problem is detected, the OEM will return the defective DSD to the manufacturer and request a replacement DSD. The DSD manufacturer may also perform a number of production line tests to detect problems prior to shipping a DSD to an OEM, as well as test a DSD when it is returned by an OEM or by a consumer.

FIG. 1A shows components of a prior art DSD in the form of a disk drive including a head 2 actuated over a disk 4 comprising a plurality of tracks 6 defined by embedded servo sectors $8_0$-$8_N$. The disk drive further comprises control circuitry 10 for demodulating a read signal 12 when reading the servo sectors $8_0$-$8_N$ and generating a position error signal (PES) of the head 2 relative to a target track 6. The PES is filtered with a suitable compensation filter to generate a control signal 14 applied to a voice coil motor 16 which rotates an actuator arm 18 to move the head 2 radially over the disk 4 in a direction that reduces the PES.

The disk drive may comprise a number of logs, such as a manufacture log 20 storing manufacturing data of the disk drive, and Self-Monitoring, Analysis, and Reporting Technology (S.M.A.R.T.) log 22 for storing diagnostic information used to for failure prediction. The disk drive may also comprise a drive self test (DST) 24 executed internally by the control circuitry 10 to quickly verify whether the disk drive is functioning correctly. However, the DST 24 performs a limited number of rudimentary tests that may not accurately detect a defect, leading to defective disk drives being installed into OEM products. Ultimately, the defective disk drives will fail while deployed in the field, leading to an expensive repair and/or return of the OEM products. Alternatively, the DST 24 or other OEM production line test may falsely detect a defective disk drive that is returned unnecessarily to the disk drive manufacturer.

BRIEF DESCRIPTION OF THE DRAWINGS

FIG. 1A shows a prior art DSD in the form of a disk drive comprising a head actuated over a disk and control circuitry.

FIG. 1B illustrates how the control circuitry of a prior art disk drive may maintain manufacturing logs and S.M.A.R.T. logs as well as execute a drive self test (DST).

FIG. 2A shows a plurality of production lines each including a plurality of test stations for testing a DSD according to an embodiment of the present invention.

FIG. 2B illustrates an embodiment of the present invention wherein when one of the test stations identifies a failed DSD, a DSD tester performs a DSD test on the DSD to verify whether it is defective before it is returned to the DSD manufacturer.

FIGS. 4A-4F shows a graphical user interface (GUI) automatically updated as DSDs are inserted, tested, and then removed from the DSD tester according to an embodiment of the present invention.

DETAILED DESCRIPTION OF EMBODIMENTS OF THE INVENTION

Figure 7A:
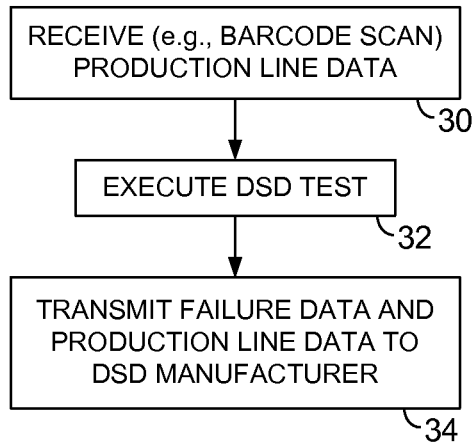
FIG. 7A is a flow diagram according to an embodiment of the present invention wherein the production line data is input via a barcode reader.

FIGS. 2A and 2B show a data storage device (DSD) tester 26 for testing a DSD $28B_2$. The DSD tester 26 comprises control circuitry operable to execute the flow diagram of FIG. 7A, wherein production line data is received through an interface (step 30), and the production line data is related to the DSD 28B$_2$. The control circuitry executes a DSD test on the DSD 28B$_2$ (step 32), and transmits failure data generated by the DSD test and the production line data to a manufacturer of the DSD 28B$_2$ (step 34). Any suitable test may be used to determine appropriate failure data. For example, some embodiments include performing tests that will be described in further detail below.

In the embodiment of FIG. 2A, a number of production lines process the DSDs in an assembly line fashion, wherein each production line comprises a plurality of test stations for performing a particular operation on the DSDs. For example, an OEM may install a DSD in the form of a disk drive or solid state drive into a suitable consumer device, such as a desktop or laptop computer. Before and/or after installing the DSD into the consumer device, a number of production line tests are performed on the DSD at various test stations. For example, a first test station may copy a test image onto the DSD, a second test station may perform various diagnostics using the test image, a third test station may install an operating system on the DSD, and a fourth test station may configure the operating system, for example, based on the country the consumer device will be sold. While at each production line test station, a problem may be detected with the DSD, such as problems identified internally by the control circuitry of the DSD (e.g., write/read errors, servoing errors, voltage regulation errors, timing errors, etc.) or errors identifying by an operator (e.g., acoustic noise of the DSD being too high, the DSD being completely non-responsive, etc.).

A DSD may fail for a number of reasons, such as defects in the components of the DSD or defects in the components of the consumer device, a defect in manufacturing the DSD, or a defect in a production line. For example, the DSD may be manufactured with a defective storage medium (e.g., defective magnetic disk) which prevents proper storage and retrieval of user data. In another example, a consumer device may be manufactured with a defective component (e.g., a fan) that may interfere with the proper operation of the DSD. In yet another example, a production line may comprise a defective assembly tool (e.g., a defective torque driver) that damages the DSD when installed into a chassis of the consumer device. In still another example, a production line may comprise a defective power supply that powers the DSD during testing.

When a DSD fails at a production line test station, rather than immediately return it to the DSD manufacturer or discard it as defective, the DSD is tested on the DSD tester 26. If the DSD passes the DSD test, it may be re-inserted back into the production line (e.g., at the beginning of the production line). If the DSD fails the DSD test, it may be discarded or returned to the manufacturer for repair. In any event, the failure data and associated production line data may be aggregated and then evaluated to identify and correct problems associated with the production line, or the manufacturing process of the DSD. For example, a defective assembly tool or power supply at a test station of a particular production line may need to be replaced to resolve the problem. In another example, the process of manufacturing a component of the DSD (e.g., storage medium, read head, semiconductor memory, etc.) may be modified in order to resolve the problem. In one embodiment, the correlation between the failure data generated by the DSD tester 26 and the production line data helps pinpoint and resolve errors that may otherwise go undetected for an extended period.

The production line data associated with a failed DSD and entered into the DSD tester 26 may comprise any suitable data, such as a production line number, and/or a test station within a production line where the DSD failed. In the embodiment of FIG. 2B, a DSD 28B$_2$ that fails during a production line test is inserted into a bay of the DSD tester 26. A chassis 36 comprising a plurality of bays receives the DSDs, wherein the chassis 36 is connected to a GUI computer comprising a desktop box 38, a monitor 40, and a keyboard 42. In one embodiment, after an operator inserts the DSD 28B$_2$ into one of the bays, the operator enters the production line data using the keyboard 42 (and/or mouse). For example, the GUI computer may display a window application comprising suitable input fields (text boxes, check boxes, drop-down menus, etc.). In addition to receiving the production line data from an operator of the DSD tester 26, the DSD tester 26 may receive configuration information from the inserted DSD 28B$_2$, such as a serial number, manufacturing logs, operating logs, etc.

Figure 3:
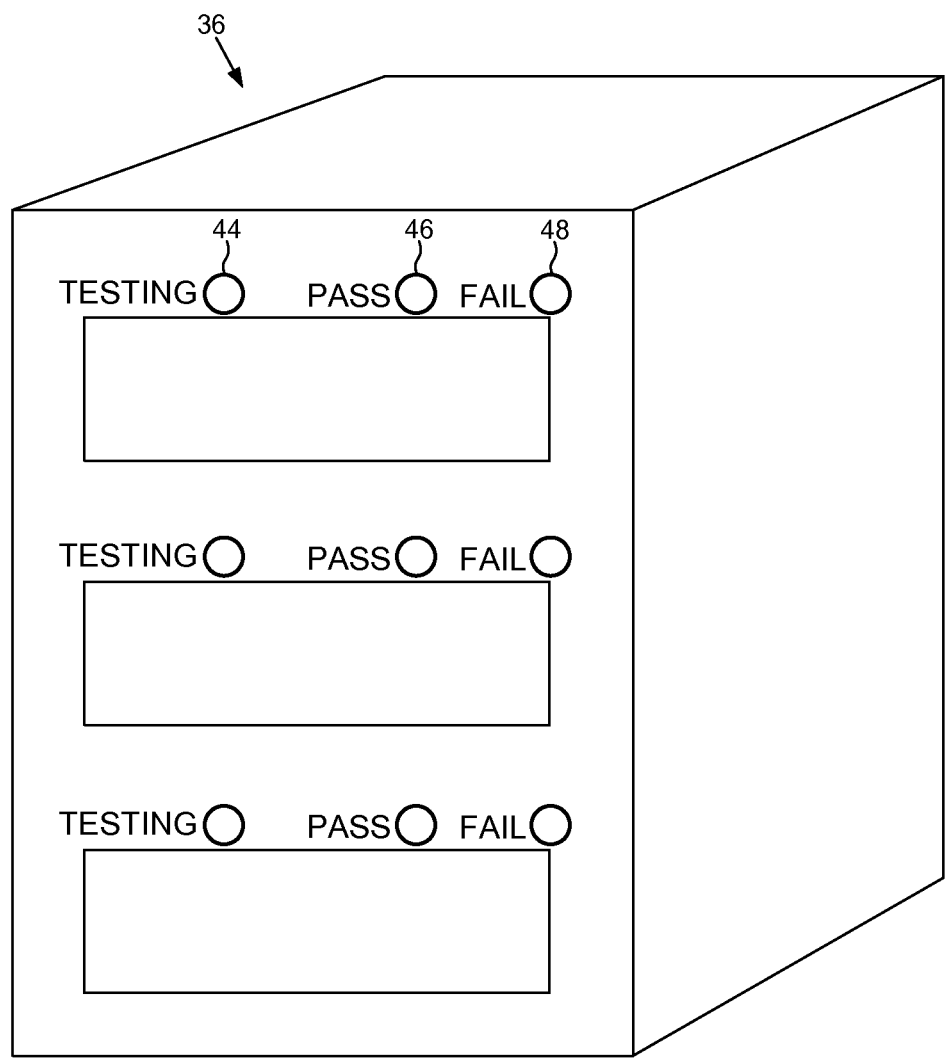
FIG. 3 shows a DSD tester comprising three bays and lights that reflect a status of the DSD tester.

FIG. 3 shows an embodiment of the present invention wherein a chassis 36 of a DSD tester comprises three bays each for receiving a DSD. In other embodiments, more or less bays may be used. In the embodiment of FIG. 3, the chassis 36 further comprises at least one light per bay for displaying a status of the DSD test. For example, the chassis 36 may comprise a first light 44 illuminated when the inserted DSD is being tested, a second light 46 illuminated when the DSD passes the test, and a third light 48 illuminated when the DSD fails the test. In other embodiments, two or more of the lights may be combined, for example, using one light to display a pass/fail status (e.g., using green and red illumination).

Figure 4C:
Figure 4D:
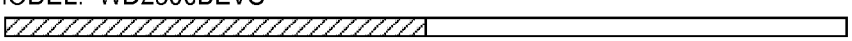
Figure 4E:
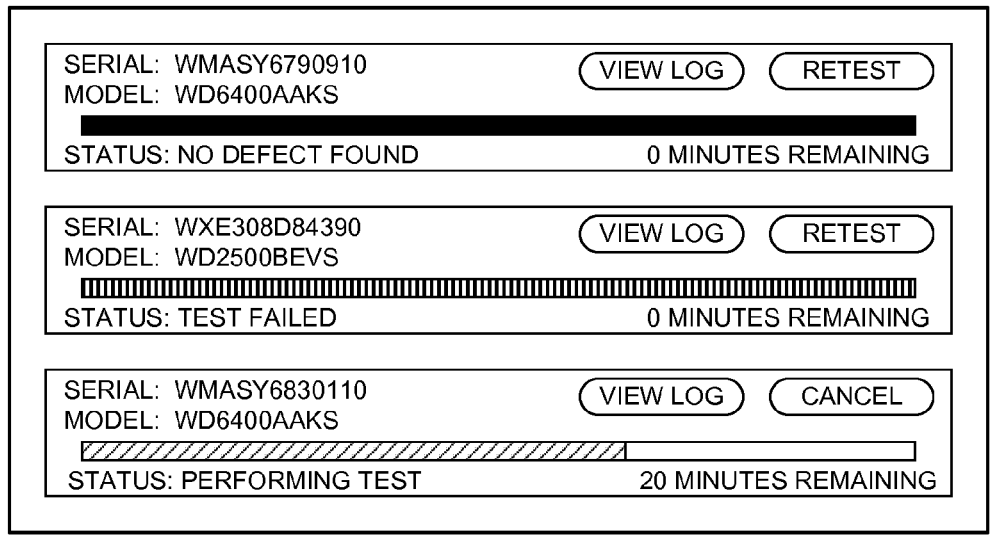
Figure 4F:
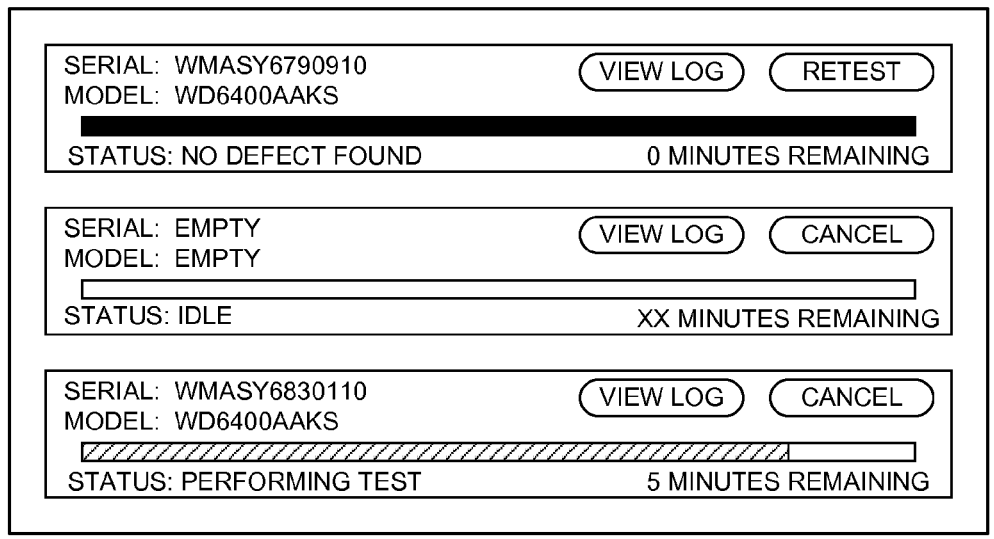

FIG. 4A shows a GUI according to an embodiment of the present invention corresponding to the three bay chassis 36 shown in FIG. 3. In this embodiment, a dialog is displayed for each bay, wherein the dialog displays a serial number/model number of the inserted DSD, a status bar showing a progress of the DSD test, a button to view a log associated with the DSD test, and a button to cancel/retry the DSD test. In one embodiment, the GUI is updated automatically when a DSD is inserted into one of the bays, and in one embodiment, the DSD test is automatically started. FIG. 4A shows an example wherein a first DSD has been inserted into the first bay, the DSD test automatically started (independent of operator input), and the GUI automatically updated to reflect the status of the DSD test. FIG. 4B shows an example wherein a second DSD has been inserted into the second bay, the GUI automatically updated, and the DSD test automatically started on the second DSD concurrent with continuing the DSD test on the first DSD. FIG. 4C shows an example wherein the GUI indicates 10 minutes remaining to test the first DSD, and 25 minutes reaming to test the second DSD. FIG. 4D shows an example wherein the DSD test on the first DSD has completed successfully, and FIG. 4E shows an example wherein the DSD test on the second DSD failed. FIG. 4E also illustrates a third DSD inserted into the third bay, the GUI automatically updated, and the DSD test automatically started and running. FIG. 4F illustrates an example wherein after the second DSD is removed from the second bay, the GUI is automatically updated to reflect that the second bay is now empty.

Figure 5:
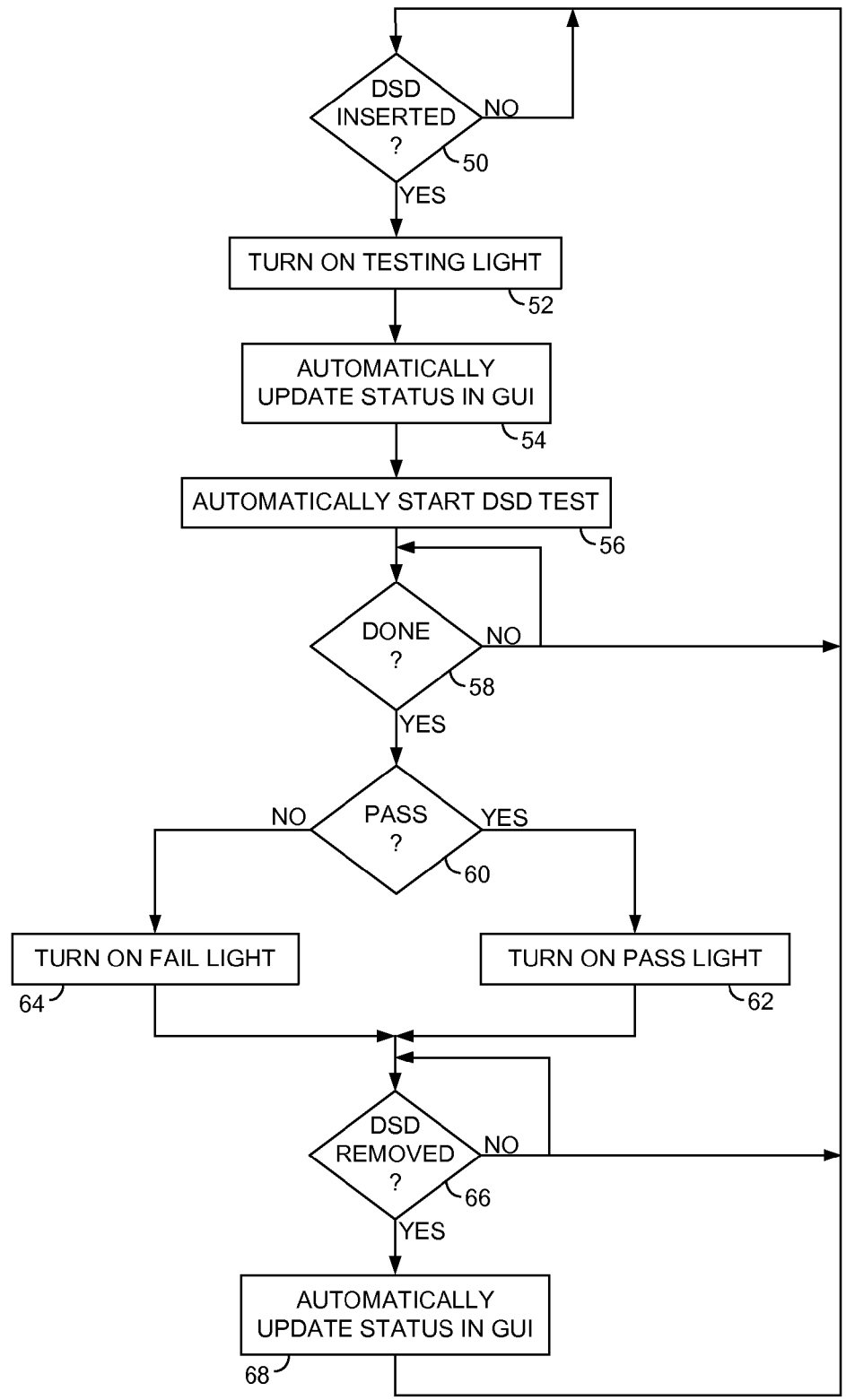
FIG. 5 is a flow diagram according to an embodiment of the present invention for automatically testing DSDs and updating a GUI as well as status lights on the DSD tester.

FIG. 5 is a flow diagram according to an embodiment of the present invention wherein when the DSD tester detects that a DSD has been inserted (or connected) (step 50), a light on the chassis of the DSD tester is controlled to indicate the DSD testing is in progress (step 52). The GUI is automatically updated independent of operator input (step 54), and the DSD test is automatically started (step 56). While testing the DSD, the flow diagram may be re-executed if another DSD is inserted (or connected). When the DSD test finishes (step 58), if the DSD passes the test (step 60) a light is controlled to indicate the test passed (step 62), and if the DSD fails the test a light is controlled to indicate the test failed (step 64). When the DSD is removed (or disconnected) (step 66), the GUI is updated automatically to reflect the change in the DSD tester (step 68). In one embodiment, the DSD tester detects that a DSD has been inserted or removed by periodically polling each bay to determine whether a DSD responds with an appropriate response.

Figure 6A:
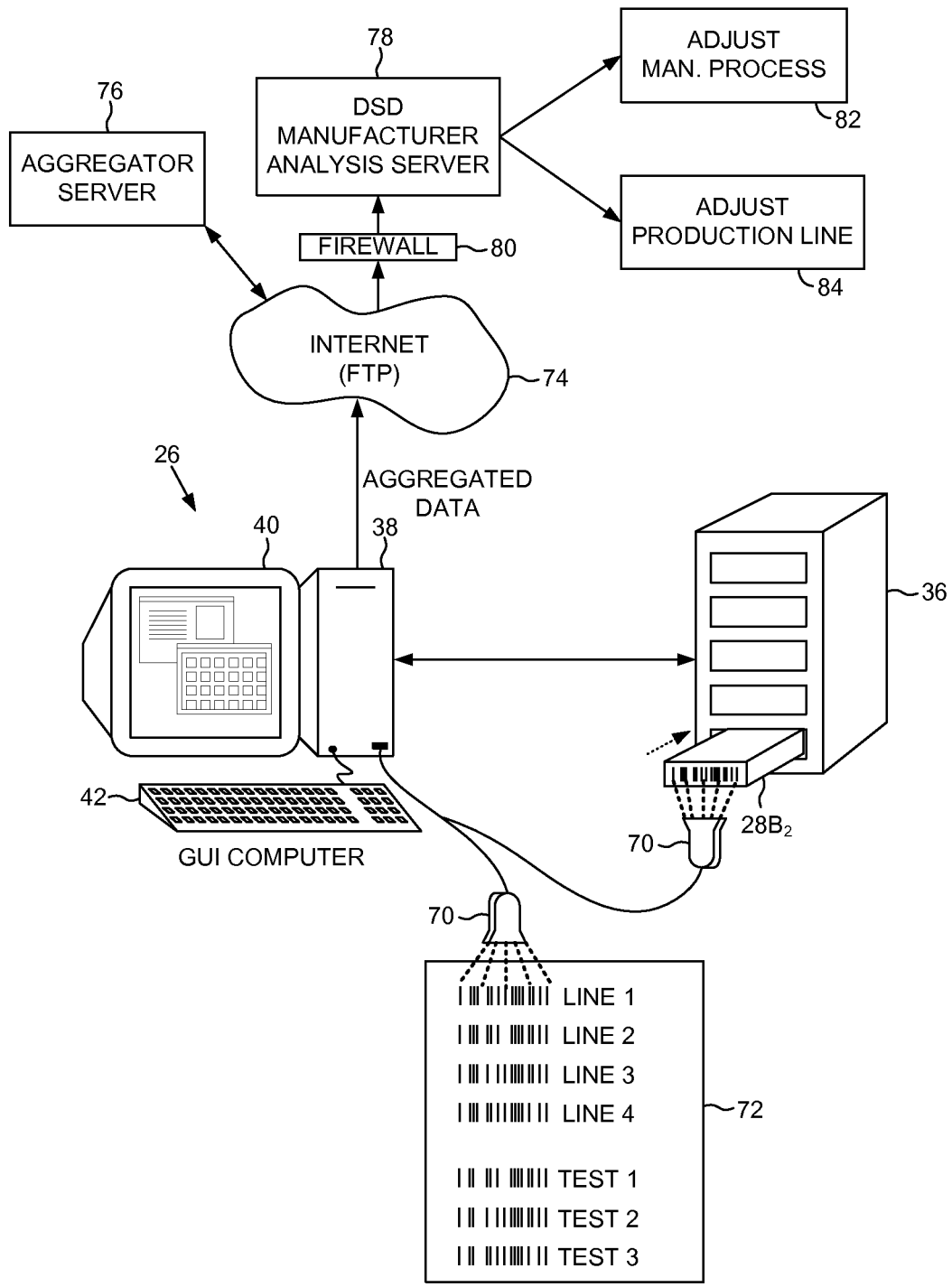
FIG. 6A shows an embodiment of the present invention wherein failure data and production line data are aggregated for a plurality of tested DSDs and the aggregated data transmitted to a manufacturer of the DSD.

FIG. 6A shows a DSD tester 26 according to an embodiment of the present invention wherein the interface for receiving the production line data comprises a barcode reader 70 for reading barcodes 72. In the example of FIG. 6A, the barcodes 72 may identify a production line number and a corresponding test station. Also in the example of FIG. 6A the barcode reader 70 may be used to read a barcode printed on the DSD 28B$_2$. For example, the barcode on the DSD 28B$_2$ may comprise a serial number or a model number, particularly in situations where the serial number or model number is not stored on the DSD 28B$_2$ or cannot be read from the DSD 28B$_2$. In one embodiment, the barcodes 72 may be printed on a sheet that remains at each DSD tester. In an alternative embodiment, the barcodes 72 may be printed on a card that is attached to a DSD immediately after it fails a production line test. For example, when an operator of a production line test station identifies a failed DSD, they may circle the appropriate barcodes corresponding to the production line and test station, and attach the card to the DSD. When the DSD is processed by the operator of the DSD tester, they scan the circled barcodes on the card in order to enter the production line data into the DSD tester.

FIG. 6A also illustrates an embodiment of the present invention wherein after testing a number of DSDs, the corresponding aggregated failure data and associated production line data is transmitted over the Internet 74 (e.g., using a File Transaction Protocol (TCP)) to an aggregator server 76. An analysis server 78 periodically checks the aggregator server 76 and downloads the DSD test data when updated. In one embodiment, the DSD test data is first analyzed to verify it is free of viruses before allowing the DSD test data through a firewall 80 that protects the analysis server 78. The analysis server 78 processes the DSD test data (e.g., correlates the failure data with the production line data) and then generates a report that can be used to modify the manufacturing process 82 for the DSD and/or to modify the production line 84.

Figure 6B:
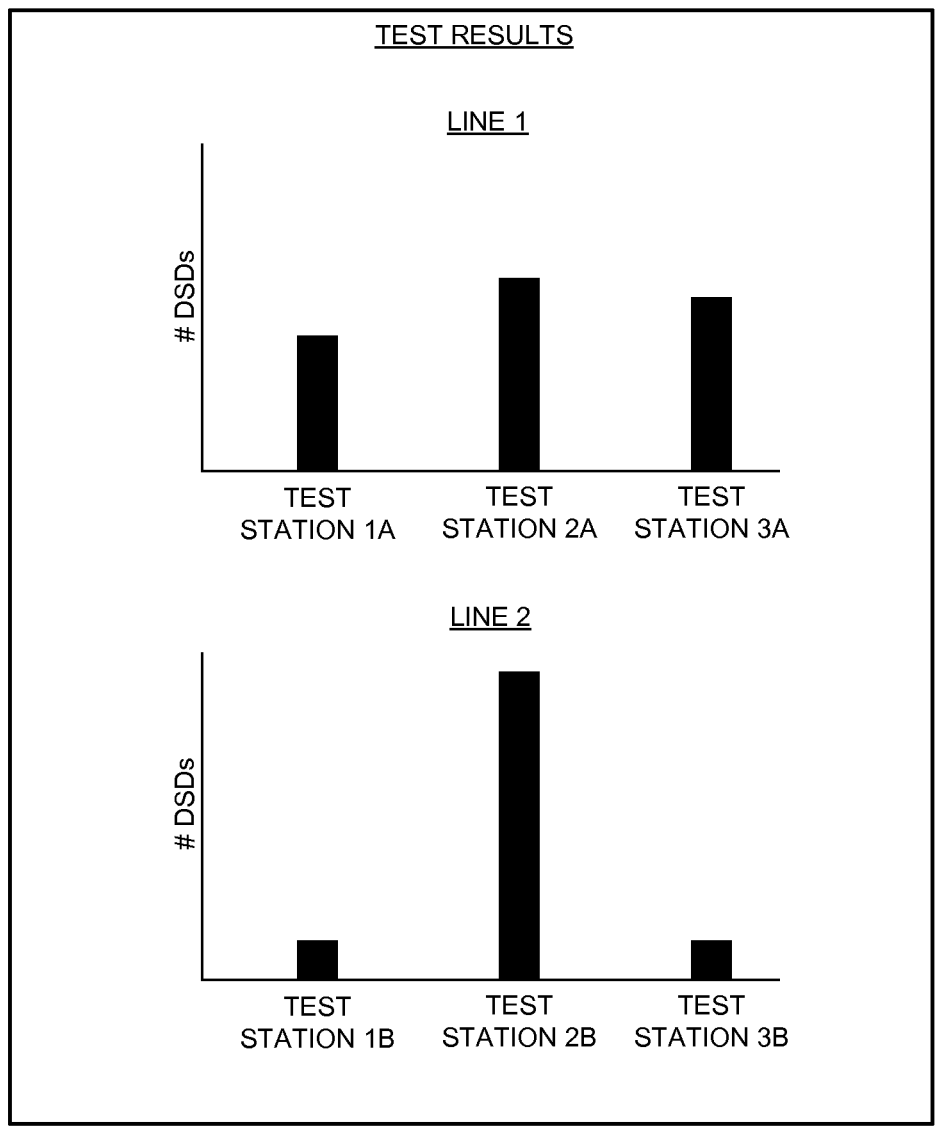
FIG. 6B shows an embodiment of the present invention wherein the failure data is correlated with the production line data, and the correlated data displayed on a screen for analysis.

FIG. 6B shows an example report that may be generated by the analysis server 78 of FIG. 6A, or alternatively generated and displayed by the DSD tester 26. In the example of FIG. 6B, a number of graphs are generated for each production line wherein the y-axis represents a number of DSDs that were processed by the DSD test and the x-axis represents each test station within the production line. The first graph in FIG. 6B shows that Line 1 generates a high number of failures at all of the test stations, which may indicate a problem with the manufacturing of the DSD rather than a problem with any test station of the production line. The second graph of FIG. 6B shows a high number of failures at Test Station 2 of Line 2 which may indicate a problem with the test station rather than with the DSDs. In one embodiment, the y-axis of the graphs may represent only the DSDs that failed the DSD test, and in an alternative embodiment, the y-axis may represent the total number of DSDs tested (regardless as to whether the DSD passed or failed the test). In yet another embodiment, different graphs may be generated that break out the correlation of passed and failed DSDs and the associated production line data. In still another embodiment, each vertical bar in the graphs of FIG. 6B may be divided into segments representing the type of failure detected by the DSD tester (e.g., write/read error, servo error, memory error, voltage supply error, etc.).

Figure 7B:
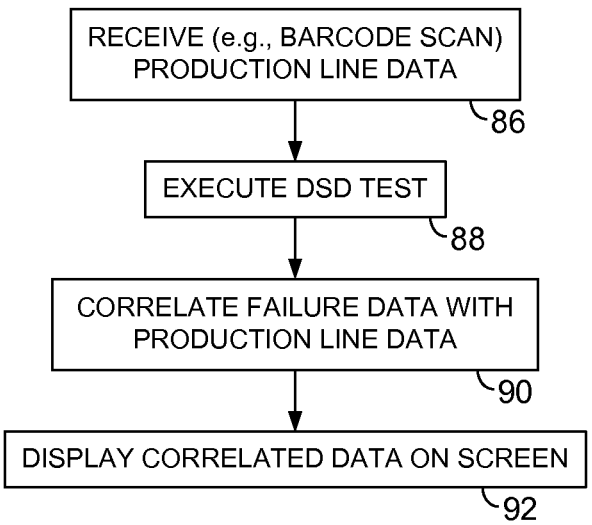
FIG. 7B is a flow diagram according to an embodiment of the present invention wherein failure data correlated with production line data is displayed on a screen.

FIG. 7B is a flow diagram according to an embodiment of the present invention wherein after receiving the production line data (step 86) and executing the DSD test (step 88), the failure data generated by the DSD test is correlated with the production line data (e.g., as shown in FIG. 6B) (step 90) and the correlated data displayed on a screen (step 92). In one embodiment, the correlated data may be displayed on a screen attached to the DSD tester 26, and in an alternative embodiment the correlated data is displayed on a screen of a remote computer (e.g., a screen of the analysis server 78 of FIG. 6A).

Figure 8:
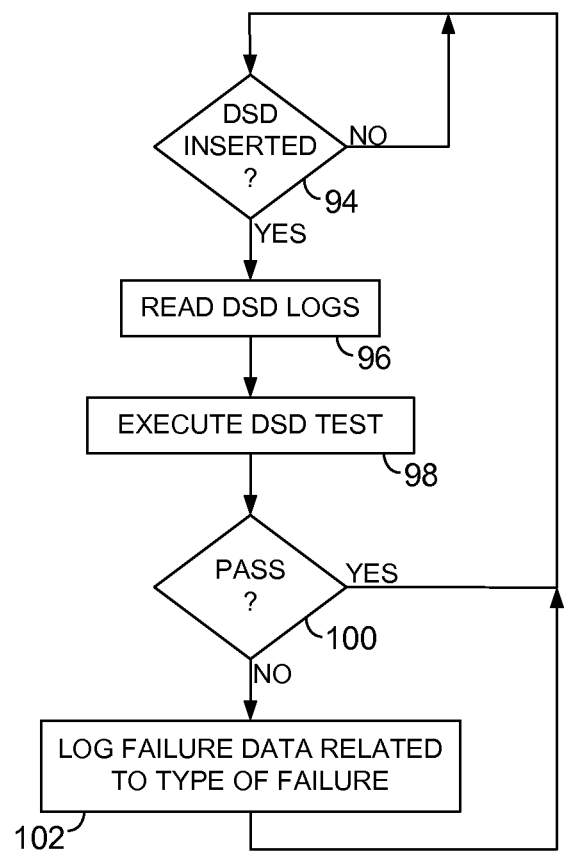
FIG. 8 is a flow diagram according to an embodiment of the present invention wherein one or more DSD logs read from the DSD are used to test the DSD.

FIG. 8 is a flow diagram executed by the control circuitry of the DSD tester 26 according to an embodiment of the present invention. When a DSD is inserted (or connected) (step 94), the DSD tester reads a DSD log from the DSD (step 96), wherein the DSD log comprises at least one entry identifying at least one error condition. When executing the DSD test (step 98) a sequence of commands associated with the error condition is executed which factors into whether the DSD passes or fails the DSD test (step 100). If the DSD fails the DSD test (step 100), the failure data related to the type of failure is logged by the DSD tester (step 102).

Figure 9:
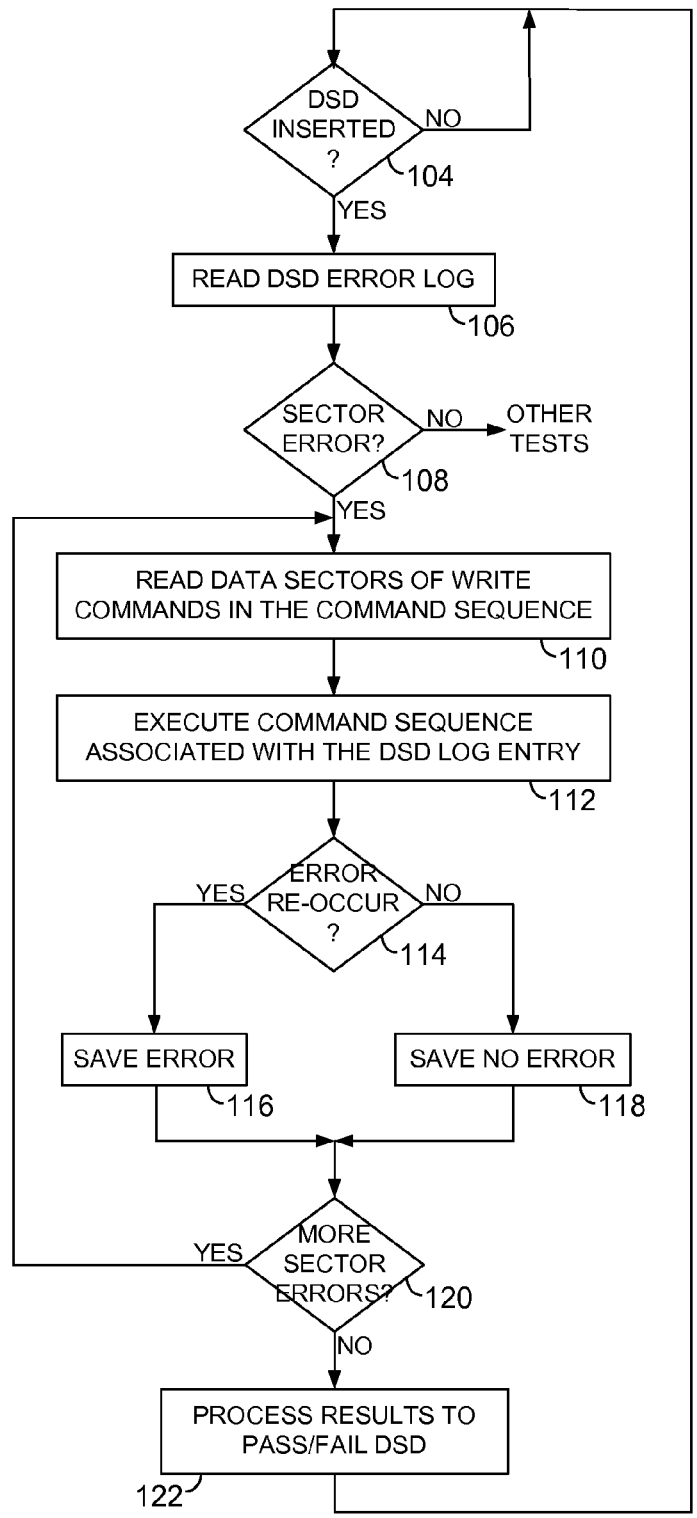
FIG. 9 is a flow diagram according to an embodiment of the present invention wherein a DSD error log identifying a command sequence associated with a read error is used to test the DSD.

FIG. 9 is a flow diagram according to an embodiment of the present invention wherein when a DSD is inserted (or connected) (step 104), the DSD tester reads a DSD error log from the DSD (step 106). If an entry in the DSD error log identifies a marginal data sector detected during a read operation (step 108), the DSD tester determines a sequence of commands to execute associated with the read error, such as a sequence of commands executed proximate the read operation when the marginal data sector was detected. The commands for reading the DSD error log from the DSD, as well as the sequence of commands transmitted to the DSD during the DSD test, may be implemented in any suitable manner, such as with a vendor specific command embedded in an Advanced Technology Attachment (ATA) command.

Before executing the sequence of commands, the DSD tester reads the data sectors that were written in the sequence of commands (step 110) so that when the write commands are re-executed, the same data can be written to the data sectors (thereby preserving the previously written data). The DSD tester then executes the sequence of commands (step 112) in an attempt to recreate the read error detected by the DSD. If the read error re-occurs (step 114), an error is saved by the DSD tester (step 116) otherwise the DSD tester saves a status of no error (step 118). After repeating this process (step 120) for all of the marginal data sectors in the DSD error log, the results of the test are evaluated to determine whether the DSD passes or fails (step 122). For example, if a predetermined percentage of read errors are recreated, or if a predetermined number of recreated errors exceeds a threshold, the DSD may be designated as failing the test.

Figure 10:
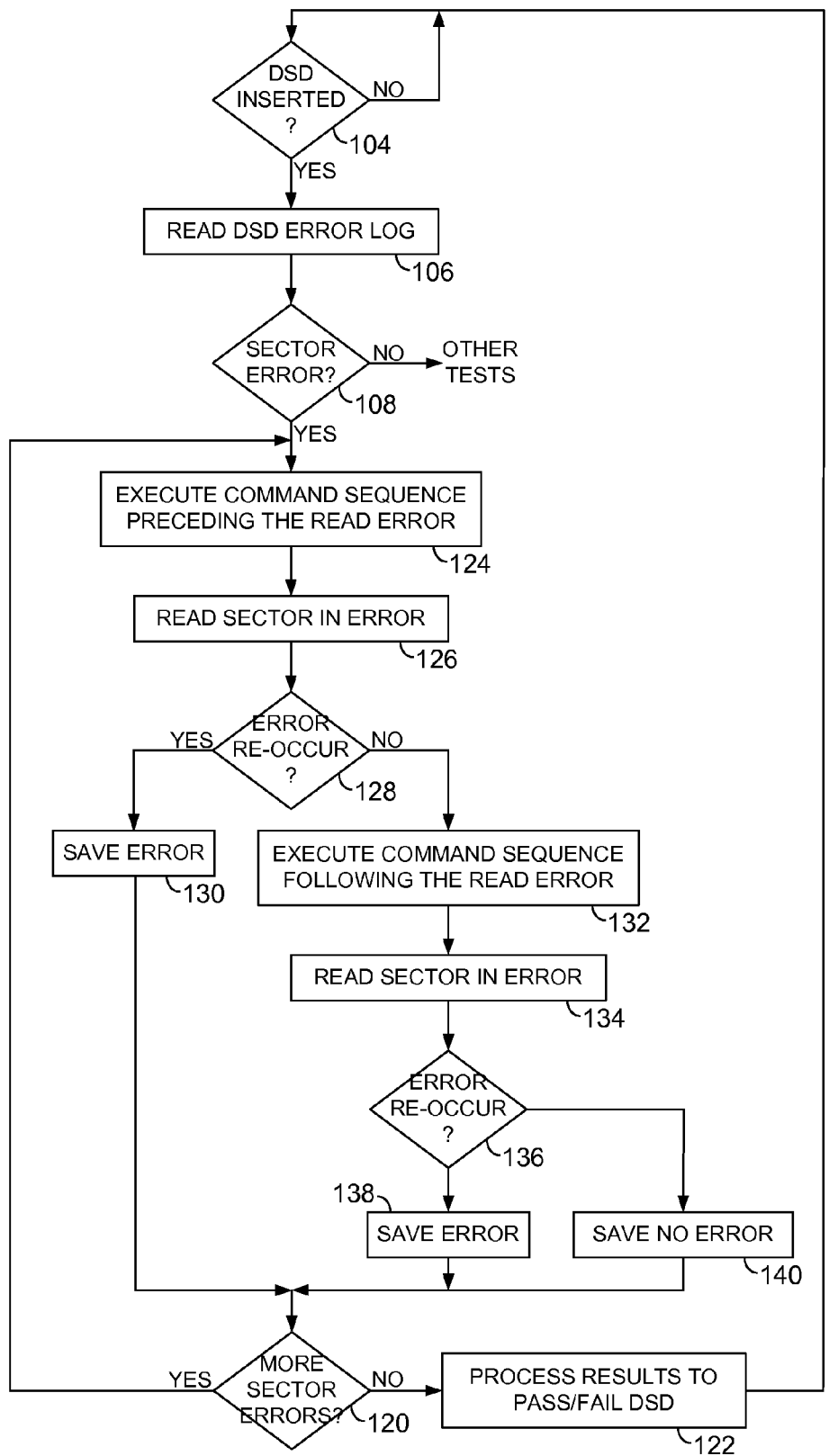
FIG. 10 is a flow diagram according to an embodiment of the present invention wherein a command sequence preceding the read error and following the read error are executed in an attempt to recreate the error.

FIG. 10 is a flow diagram according to an embodiment of the present invention which extends on the flow diagram of FIG. 9, wherein the DSD tester executes a sequence of commands preceding the read error (step 124) and then reads the marginal data sector (step 126). If the error is recreated (step 128), an error is saved (step 130). Otherwise, the DSD tester executes a sequence of commands following the read error (step 132) and then reads the marginal data sector (step 134). If the error is recreated (step 136), an error is saved (step 138), otherwise a status of no error is saved (step 140). Executing a sequence of commands preceding and following the read error may recreate the error, for example, if the sequence of commands includes write commands that cause adjacent track interference (ATI). Alternatively, executing the sequence of commands may identify an error that does not occur in normal operation, such as a firmware bug that only manifests itself when a given sequence of commands is executed while each individual command alone would not cause an error condition.

Figure 11:
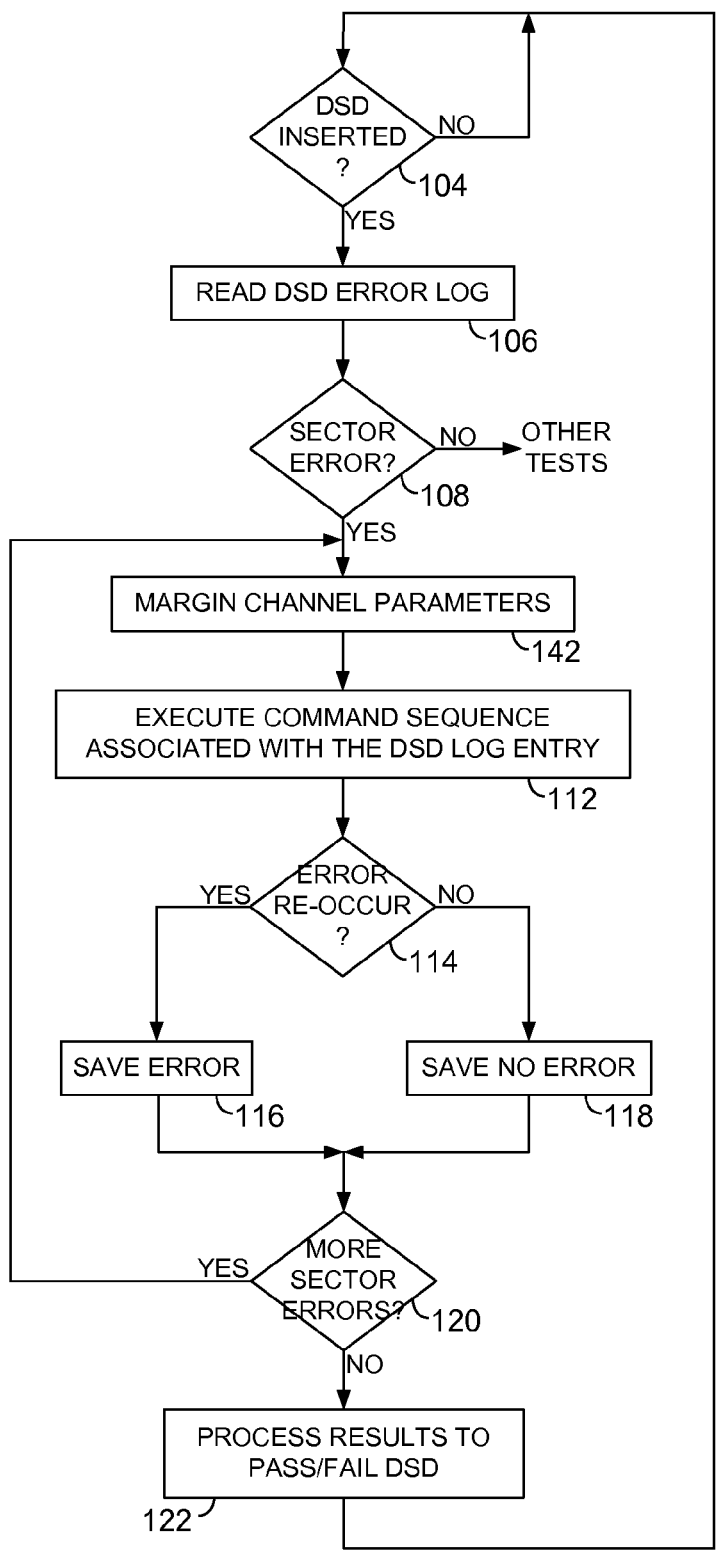
FIG. 11 is a flow diagram according to an embodiment of the present invention wherein channel parameters of the DSD are margined when executing the command sequence during the DSD test.

FIG. 11 is a flow diagram according to an embodiment of the present invention which extends on the flow diagram of FIG. 9, wherein the DSD tester margins channel parameters (step 142) prior to executing the sequence of commands (step 112) in order to increase the likelihood of recreating the read error. Any suitable channel parameters may be margined, such as increasing a fly-height of a write element and/or read element, decreasing a write current or voltage, decreasing a read current or voltage, adding a tracking error, adding noise or an offset to a read signal, adjusting a supply voltage, adding timing jitter, etc. Margining channel parameters to recreate an error may provide insight into what caused the error before the DSD was coupled with the DSD tester. For example, a problem with an OEM line (e.g., too much vibration) may be identified if a number of DSDs from the OEM line are identified as creating a similar type of error when the same channel parameters are margined in the same way.

Figure 12:
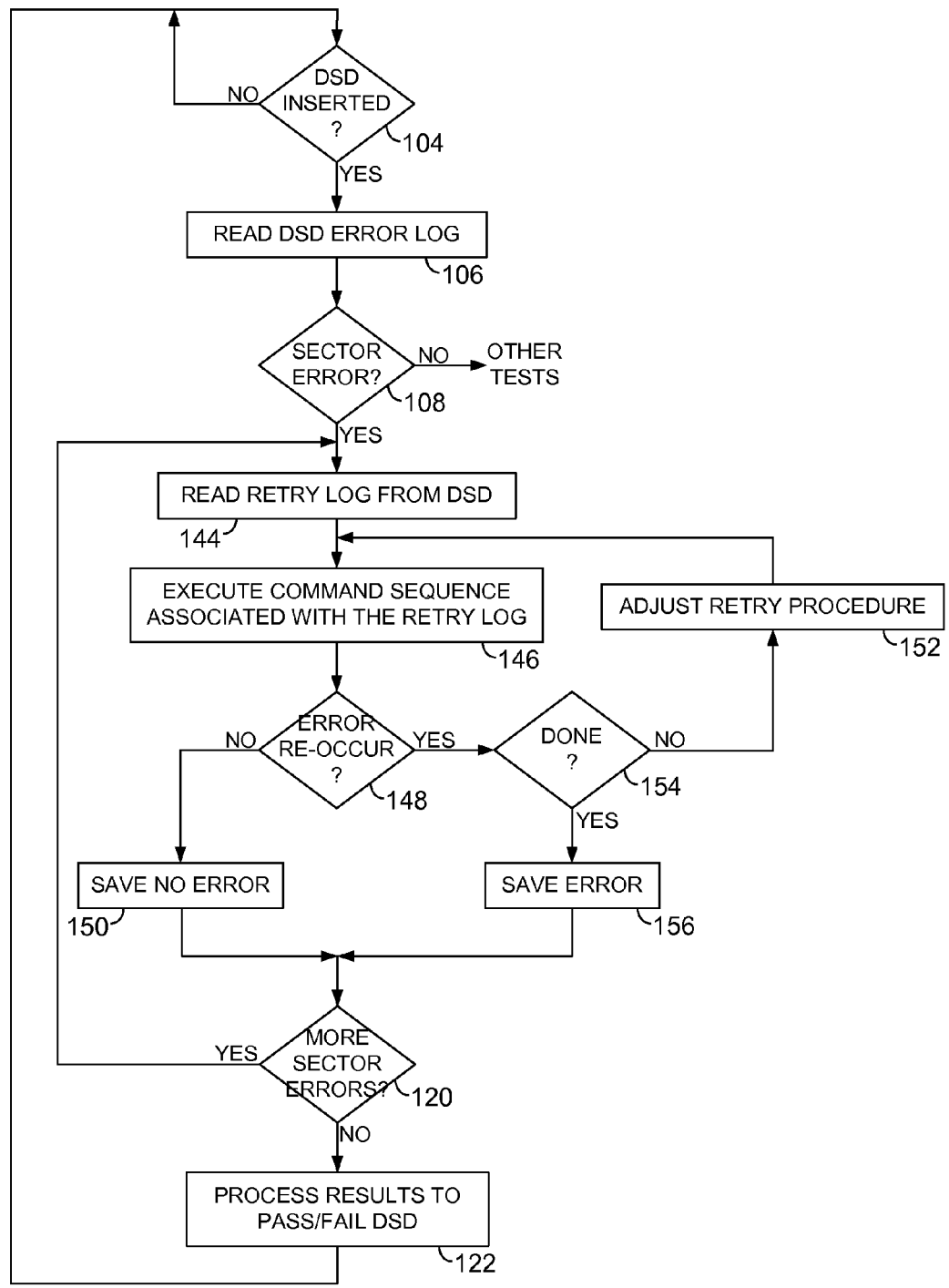
FIG. 12 is a flow diagram according to an embodiment of the present invention wherein the command sequence comprises commands executed during a retry operation.

FIG. 12 is a flow diagram according to an embodiment of the present invention which extends on the flow diagram of FIG. 9, wherein the DSD tester reads a retry log from the DSD (step 144) associated with the marginal data sector. That is, when the DSD detected the marginal data sector, it may have executed a retry procedure in an attempt to recover the data sector. In one embodiment, an entry is created in the DSD error log if the marginal data sector could not be recovered using the retry procedure. The DSD tester then re-executes the same retry procedure (step 146) as part of the DSD test. If the error does not re-occur (i.e., if the data sector is recoverable) (step 148), then a status of no error is saved (step 150). If the error re-occurs (step 148), the DSD tester may adjust the retry procedure, for example, by lengthening a number of iterations during a particular step of the retry procedure, or by adjusting the order of steps executed during the retry procedure. The retry procedure may be adjusted several times wherein the marginal data sector may eventually be recovered, or deemed unrecoverable (step 154) and a corresponding error saved (step 156). In one embodiment, the retry procedure adjusted at step 152 may be used to modify the retry procedure of the DSD under test and/or to adjust the retry procedures of all manufactured DSDs (i.e., the re-optimized retry procedure may be transmitted to the DSD manufacturer where it is used to modify the manufacturing process of the DSDs).

Figure 13:
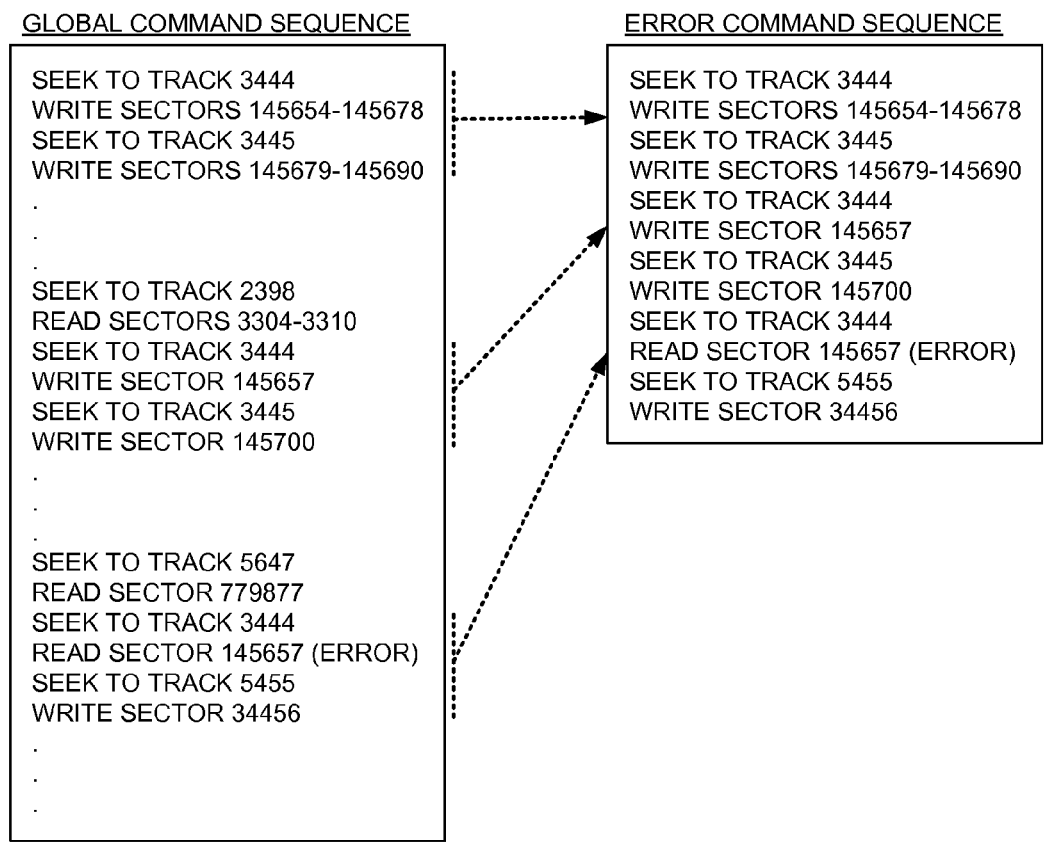
FIG. 13 shows an embodiment of the present invention wherein the command sequence executed during the DSD test is generated by aggregating subsets of a global command sequence.

FIG. 13 illustrates an embodiment of the present invention wherein the DSD maintains a global log identifying a plurality of sequential commands executed by the DSD. For example, the global log may save the last several commands executed by the DSD (hundreds or even thousands of commands). The sequence of commands associated with a read error in the DSD error log comprises at least two subsets of the sequential commands identified by the global log. In the example of FIG. 13, a read error is detected when attempting to read data sector 145657. Accordingly, the DSD tester constructs a sequence of commands from the global log by aggregating several subsets that may have contributed to the read error. In the example of FIG. 13, the DSD tester extracts two subsets of previously executed write commands that may have contributed to the read error (e.g., due to ATI). The DSD tester then re-executes the command sequence in an attempt to recreate the read error as described above.

Figure 14A:
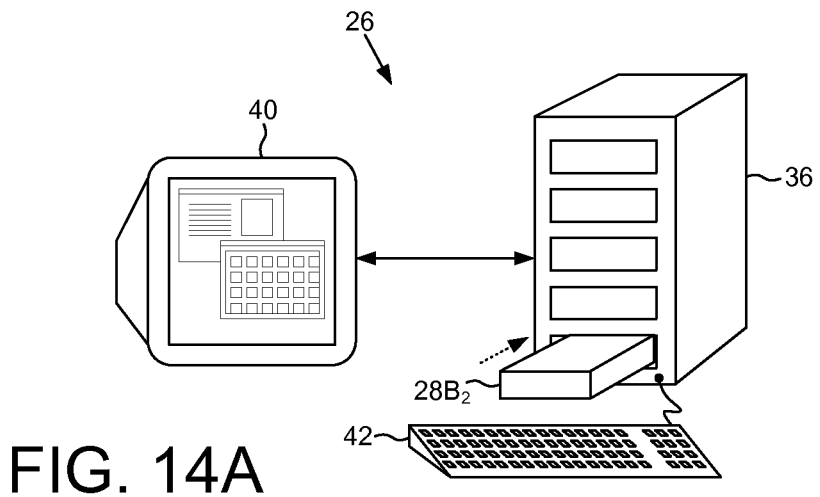
FIG. 14A shows an embodiment of the present invention wherein the DSD tester comprises a chassis interfacing with a screen.

The DSD tester 26 employed in the embodiments of the present invention may comprise any suitable configuration. FIG. 14A shows a DSD tester 26 according to an embodiment wherein a chassis 36 comprising a plurality of bays may also comprise the control circuitry for implementing the test procedures (e.g., a microprocessor executing code segments of a control program stored on a computer readable storage medium). The control circuitry within the chassis 36 may also interface with a monitor 40 for displaying the results of the DSD test.

Figure 14B:
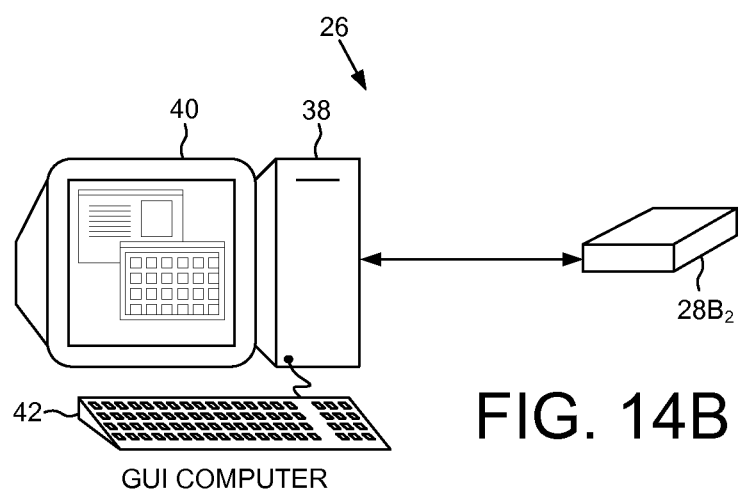
FIG. 14B shows an embodiment of the present invention wherein the DSD tester interfaces with the DSD using a suitable cable connection (e.g., Universal Serial Bus (USB)).

FIG. 14B shows an embodiment of the present invention wherein the DSD $28B_2$ is connected to the DSD tester 26 using a suitable cable (e.g., a USB cable) rather than inserted into a bay. In one embodiment, the DSD tester 26 may comprise a plurality of cables and input ports for connecting and simultaneously testing a plurality of DSDs (similar to the embodiment employing a plurality of bays).

Figure 14C:
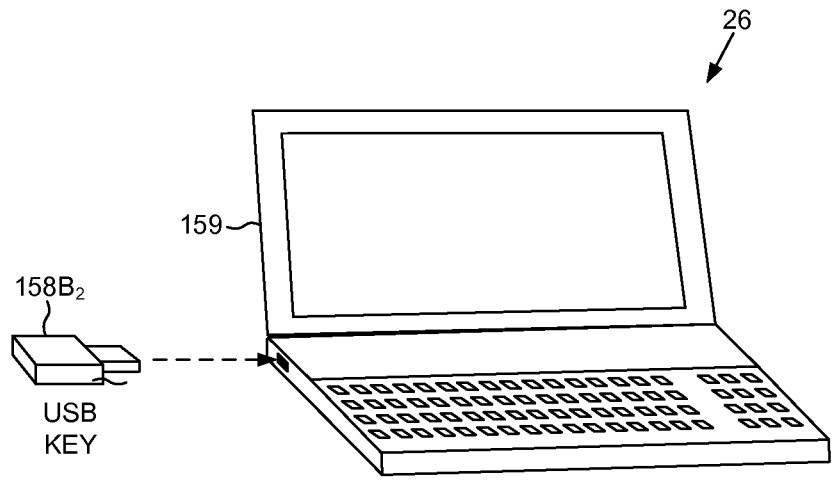
FIG. 14C shows an embodiment of the present invention wherein the DSD tester comprises a USB key that is plugged into an OEM product to perform the DSD test.

FIG. 14C shows an embodiment of the present invention wherein the DSD tester 26 comprises a USB key $158B_2$ for storing the code segments of the DSD test. FIG. 14C also illustrates an embodiment wherein the DSD tester 26 comprises a consumer device 159 being assembled in a production line. The USB key $158B_2$ is plugged into the consumer device 159 which reads the DSD test from the USB key, executes the DSD test, and alternatively displays the results of the DSD test. In the example of FIG. 14C, the consumer device 159 comprises a laptop computer including an internal DSD (e.g., a disk drive or solid state drive), keyboard, and a screen, wherein the DSD test stored on the USB key $158B_2$ is used to test the internal DSD. In one embodiment, the operator configures the laptop to boot from the USB key $158B_2$ (e.g., by pressing a key on the keyboard of the laptop) rather than boot from the internal DSD. The operator (of the laptop) then executes the DSD test from the USB key $158B_2$.

In one embodiment, a USB key is assigned to each test station within each production line, wherein the production line data is stored on each USB key (e.g., in a file). When the operator of an OEM test station identifies a failed DSD, they plug in the USB key and execute the DSD test. The results of the DSD test are stored on the USB key and later evaluated using an analysis computer (e.g., a local computer at the production line site, or the test results transmitted to an analysis server of the DSD manufacturer). The analysis computer processes the test results from the USB key as well as the production line data from the USB key so that the test results can be correlated with the production line (e.g., as shown in FIG. 6B). In another embodiment, the USB key $158B_2$ may prompt the user to input production line data via the consumer device 159 (FIG. 14C), which is then stored on USB key $158B_2$. In yet another embodiment, the USB key $158B_2$ may be used by a customer return center to perform non-destructive tests on a returned consumer device.

In one embodiment, the USB key $158B_2$ is plugged into a Universal Serial Bus port of the consumer device 159. However, the USB key $158B_2$ may implement any suitable communication protocol and therefore be plugged into any suitable port of the consumer device (e.g., a Firewire port, SCSI port, IDE port, etc.). Therefore, the term "USB key" should be interpreted as a generic identifier for identifying any suitable storage device (e.g., hard disk drive, solid state drive) using any type of suitable interface protocol (e.g., Firewire, SCSI, IDE, Bluetooth, etc.).

Figure 15:
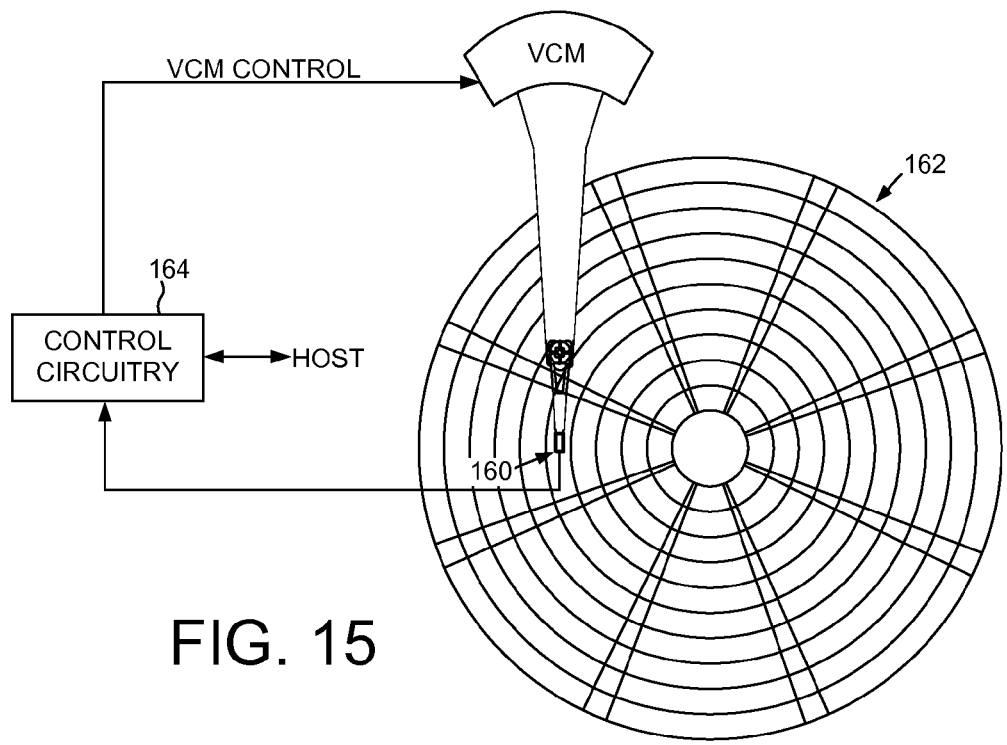
FIG. 15 shows an embodiment of the present invention wherein the DSD comprises a disk drive.
Figure 16:
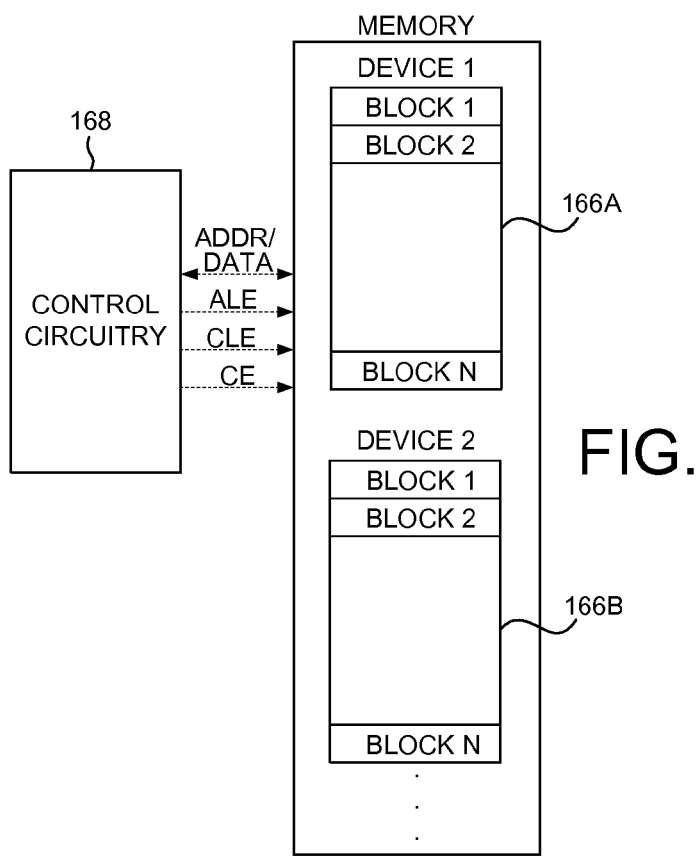
FIG. 16 shows an embodiment of the present invention wherein the DSD comprises a solid state drive.

The embodiments of the present invention may be employed in any suitable DSD comprising any suitable storage medium, such as a magnetic medium, optical medium, or semiconductor medium. FIG. 15 shows a DSD comprising a disk drive including a head 160 actuated over a disk 162 and control circuitry 164. FIG. 16 shows a solid state drive comprising a plurality of non-volatile semiconductor memories 166A, 166B, etc., such as flash memories, and control circuitry 168. A hybrid data storage device may also be employed comprising components of a disk drive shown in FIG. 15 combined with the non-volatile semiconductor memories shown in FIG. 16.

In one embodiment, the DSD tester is employed in an OEM production line that installs a DSD into a consumer device (desktop or laptop computer, smartphone, digital video recorder, etc.). In another embodiment, hub facilities of the DSD manufacturer may test DSDs in the field that were received from the factory, prior to sending the DSD to an OEM. Such testing may identify problem areas in the factory and/or supply chain before the DSD is shipped to the OEM. In yet another embodiment, the DSD manufacturer may use the DSD tester to test DSDs when they are returned from an OEM or from a consumer.

What is claimed is:

1. A data storage device (DSD) tester for testing a DSD, the DSD tester comprising control circuitry operable to:
   receive production line data from the DSD through an interface, wherein the production line data identifies at least part of the DSD;
   execute a DSD test on the DSD; and
   transmit failure data generated by the DSD test and the production line data to a failure information database.

2. The DSD tester as recited in claim 1, wherein the failure information database is located on a remote server accessible over the Internet.

3. The DSD tester as recited in claim 1, wherein the interface comprises a barcode reader.

4. The DSD tester as recited in claim 1, wherein the production line data comprises a serial number of the DSD.

5. The DSD tester as recited in claim 4, wherein the interface comprises a barcode reader for reading the serial number from an enclosure of the DSD.

6. The DSD tester as recited in claim 1, wherein the control circuitry is further operable to:
   aggregate the failure data and the production line data for a plurality of DSDs; and
   transmit the aggregated data to the manufacturer of the DSD in an atomic operation.

7. The DSD tester as recited in claim 1, wherein the control circuitry is further operable to transmit the failure data and the production line data to the manufacturer of the DSD using a File Transfer Protocol (FTP).

8. The DSD tester as recited in claim 1, further comprising a plurality of bays, wherein the control circuitry is further operable to detect when the DSD has been inserted into one of the bays.

9. The DSD tester as recited in claim 1, further comprising a Universal Serial Bus (USB) key operable to plug into a USB port of a consumer device.

10. The DSD tester as recited in claim 1, wherein the DSD comprises a disk.

11. The DSD tester as recited in claim 1, wherein the DSD comprises a semiconductor memory.

12. A data storage device (DSD) tester for testing a DSD, the DSD tester comprising a screen and control circuitry operable to:
   receive production line data from the DSD through an interface, the production line data identifies at least part of the DSD;
   execute a DSD test on the DSD;
   correlate failure data generated by the DSD test with the production line data to generate correlated data; and
   display the correlated data on the screen.

13. The DSD tester as recited in claim 12, wherein the interface comprises a barcode reader.

14. The DSD tester as recited in claim 12, wherein the production line data comprises a serial number of the DSD.

15. The DSD tester as recited in claim 14, wherein the interface comprises a barcode reader for reading the serial number from an enclosure of the DSD.

16. The DSD tester as recited in claim 12, further comprising a plurality of bays, wherein the control circuitry is further operable to detect when the DSD has been inserted into one of the bays.

17. The DSD tester as recited in claim 12, wherein the DSD comprises a disk.

18. The DSD tester as recited in claim 12, wherein the DSD comprises a semiconductor memory.

19. A method of processing test data received from a data storage device (DSD) tester after testing a DSD, the method comprising:
   receiving production line data from the DSD, wherein the production line data identifies at least part of the DSD;
   receiving failure data generated by the DSD tester after testing the DSD; and
   correlating the failure data with the production line data to generate correlated data that identifies an error in the production line.

20. The method as recited in claim 19, wherein the production line data and the failure data are received over the Internet.

21. The method as recited in claim 20, wherein the production line data and the failure data are received using a File Transfer Protocol (FTP).

22. The method as recited in claim 19, further comprising displaying the correlated data on a screen.

23. The method as recited in claim 19, further comprising adjusting a DSD manufacturing process in response to the correlated data.

24. The method as recited in claim 23, wherein the manufacturing process is adjusted after analyzing correlated data generated for a plurality of DSDs.

25. The method as recited in claim 19, further comprising adjusting a production line in response to the correlated data.

26. The method as recited in claim 25, wherein the production line is adjusted after analyzing correlated data generated for a plurality of DSDs.

27. The method as recited in claim 19, wherein the DSD comprises a disk.

28. The method as recited in claim 19, wherein the DSD comprises a semiconductor memory.

29. A method of testing a data storage device (DSD), the method comprising:
   receiving production line data from the DSD, wherein the production line data identifies at least part of the DSD;
   executing a DSD test on the DSD; and
   transmitting failure data generated by the DSD test and the production line data to a failure information database.

30. The method as recited in claim 29, wherein the failure information database is located on a remote server accessible over the Internet.

31. The method as recited in claim 29, further comprising reading the production line data from the DSD with a barcode reader.

32. The method as recited in claim 29, wherein the production line data comprises a serial number of the DSD.

33. The method as recited in claim 32, further comprising reading a barcode representing the serial number from an enclosure of the DSD.

34. The method as recited in claim 29, further comprising:
   aggregating the failure data and the production line data for a plurality of DSDs; and transmitting the aggregated data to the manufacturer of the DSD in an atomic operation.

35. The method as recited in claim 29, further comprising transmitting the failure data and the production line data to the manufacturer of the DSD using a File Transfer Protocol (FTP).

36. The method as recited in claim 29, further comprising detecting when the DSD has been inserted into a bay.

37. The method as recited in claim 29, further comprising plugging a Universal Serial Bus (USB) key into a USB port of a consumer device.

38. The method as recited in claim 29, wherein the DSD comprises a disk.

39. The method as recited in claim 29, wherein the DSD comprises a semiconductor memory.

40. A method of testing a data storage device (DSD), the method comprising:
    receiving production line data from the DSD, wherein the production line data identifies at least part of the DSD;
    executing a DSD test on the DSD;
    correlate failure data generated by the DSD test with the production line data to generate correlated data; and
    displaying the correlated data on a screen.

41. The method as recited in claim 40, further comprising reading the production line data from the DSD with a barcode reader.

42. The method as recited in claim 40, wherein the production line data comprises a serial number of the DSD.

43. The method as recited in claim 42, further comprising reading a barcode representing the serial number from an enclosure of the DSD.

44. The method as recited in claim 40, further comprising detecting when the DSD has been inserted into a bay.

45. The method as recited in claim 40, wherein the DSD comprises a disk.

46. The method as recited in claim 40, wherein the DSD comprises a semiconductor memory.

47. A data storage device (DSD) tester for testing a DSD, the DSD tester comprising a plurality of bays and control circuitry operable to:
    detect when the DSD has been inserted into one of the bays;
    receive production line data through an interface, wherein the production line data is related to the DSD;
    execute a DSD test on the DSD; and
    transmit failure data generated by the DSD test and the production line data to a failure information database.

48. A data storage device (DSD) tester for testing a DSD, the DSD tester comprising a Universal Serial Bus (USB) key operable to plug into a USB port of a consumer device and control circuitry operable to:
    receive production line data through an interface, wherein the production line data is related to the DSD;
    execute a DSD test on the DSD; and
    transmit failure data generated by the DSD test and the production line data to a failure information database.

49. A method of testing a data storage device (DSD), the method comprising:
    detecting when the DSD has been inserted into a bay;
    receiving production line data related to the DSD;
    executing a DSD test on the DSD; and
    transmitting failure data generated by the DSD test and the production line data to a failure information database.

50. A method of testing a data storage device (DSD), the method comprising:
    plugging a Universal Serial Bus (USB) key into a USB port of a consumer device;
    receiving production line data related to the DSD;
    executing a DSD test on the DSD; and
    transmitting failure data generated by the DSD test and the production line data to a failure information database.

* * * * *